United States Patent [19]

Takaishi et al.

[11] Patent Number: 4,465,869

[45] Date of Patent: Aug. 14, 1984

[54] PROCESS FOR THE PRODUCTION OF GLYCERYL ETHERS

[75] Inventors: Naotake Takaishi, Utsunomiya; Kouichi Urata, Ichikai; Yoshiaki Inamoto, Utsunomiya, all of Japan

[73] Assignee: Kao Corporation, Tokyo, Japan

[21] Appl. No.: 399,296

[22] Filed: Jul. 19, 1982

Related U.S. Application Data

[63] Continuation of Ser. No. 240,948, Mar. 5, 1981, abandoned.

[30] Foreign Application Priority Data

Mar. 21, 1980 [JP] Japan .................................. 55-36348

[51] Int. Cl.³ ..................... C07C 41/00; C07D 317/00
[52] U.S. Cl. ................................... 568/672; 549/453; 568/675
[58] Field of Search ................. 549/453; 568/672, 675

[56] References Cited

U.S. PATENT DOCUMENTS

| | | | |
|---|---|---|---|
| 2,028,403 | 1/1936 | Mares ................................ | 260/340.7 |
| 2,038,705 | 4/1936 | Baldwin et al. ................... | 260/340.7 |
| 2,156,724 | 5/1939 | Evans et al. ........................ | 568/672 |
| 2,197,467 | 4/1940 | Evans et al. ........................ | 568/672 |
| 3,629,287 | 12/1971 | Hardie et al. ....................... | 549/453 |
| 3,725,438 | 4/1973 | Barone et al. ...................... | 549/453 |

FOREIGN PATENT DOCUMENTS

| | | | |
|---|---|---|---|
| 6166186 | 12/1981 | Japan ................................. | 549/453 |
| 8008078 | 1/1983 | Japan ................................. | 549/453 |
| 784225 | 10/1957 | United Kingdom ............... | 549/452 |

*Primary Examiner*—Ethel G. Love
*Attorney, Agent, or Firm*—Oblon, Fisher, Spivak, McClelland & Maier

[57] ABSTRACT

The specification describes a process for the production of a 4-alkoxymethyl-1,3-dioxolan in good yield, in high purity and in a simple manner by reacting an alkyl glycidyl ether with a carbonyl compound in the presence of an acid catalyst. The 4-alkoxymethyl-1,3-dioxolan is useful as an intermediate for the production of an α-monoalkyl glyceryl ether by hydrolysis.

1 Claim, No Drawings

PROCESS FOR THE PRODUCTION OF GLYCERYL ETHERS

This is a continuation of application Ser. No. 240,948, filed Mar. 5, 1981, now abandoned.

BACKGROUND OF THE INVENTION

1. Field of the Invention

The present invention relates to a process for the production of a dioxolan from an alkyl glycidyl ether, and a process for the production of a glyceryl ether from this dioxolan.

2. Description of the Prior Art

As α-monoalkyl glyceryl ethers, there have hitherto been known palmityl glyceryl ether (i.e. Chimyl alcohol) which is present in the lipids of fish, stearyl glyceryl ether (i.e. Batyl alcohol) and oleyl glyceryl ether (i.e. Serachyl alcohol). And it is known that they exhibit excellent performance as an emulsifier, particularly as a W/O type emulsified (Japanese Laid-open Patent Applications Nos. 92239/74, 12109/77, and 87612/74). Also they are known to have pharmacological activities such as stimulating effects for the formation of blood cells in the bone marrow, anti-inflammatory effects and anti-tumor activities (Japanese Patent Publications Nos. 10724/74, and 18171/77). The following two methods are known for the production of these α-monoalkyl glyceryl ethers from the corresponding alcohols.

(1) An alcohol is converted into an alkylhalide, which is then reacted with a glycerol alkali metal alcoholate having hydroxyl groups protected, thereby to obtain a 4-alkoxymethyl 1,3-dioxolan, which is then hydrolyzed. The reactions are represented by the following formulae:

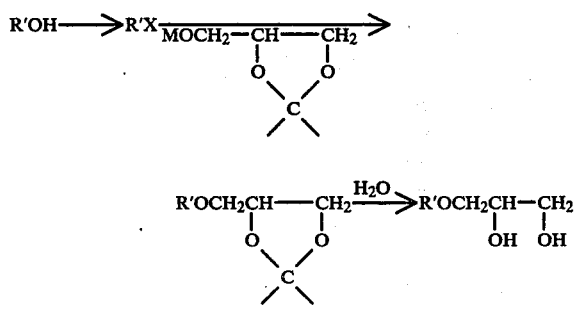

(where R' is an alkyl group, etc, X is a halogen, and M is an alkali metal).

(2) An alkyl glycidyl ether is produced from an alcohol and an epihalohydrin, and it is then hydrolyzed. The reactions are represented by the following formulae.

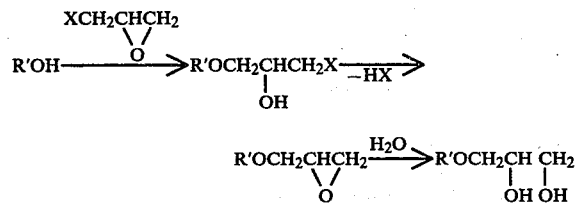

(where R' is as defined above, and X is a halogen).

These methods have the following drawbacks and accordingly they are not entirely satisfactory.

Namely, in the method (1), although the hydrolysis of the 4-alkoxymethyl-1,3-dioxolan to the glyceryl ether proceeds almost quantitatively, it is difficult to produce the dioxolan on an industrial scale. (i) Firstly, an alkylhalide must be prepared from an alcohol. It is, however, difficult to produce an alkylhalide containing an unsaturated bond on an industrial scale. (ii) Although the glycerol compound having the hydroxyl group protected (4-hydroxymethyl-1,3-dioxolan) can be synthesized from glycerine and a carbonyl compound in the presence of an acid catalyst, it takes a long period of time for the reaction, which is a dehydration reaction and accordingly requires a great amount of a dehydrating agent. (iii) In the reaction system for the condensation reaction of the alkylhalide and the alkali metal alcoholate of 4-hydroxymetyl-1,3-dioxolan, there exists a strong base and a part of the alkylhalide is thereby subjected to dehydrohalogenation reaction to form a terminal olefin, whereby the yield of the intended 4-alkoxymethyl-1,3-dioxolan is reduced.

With respect to the method (2), certain processes have recently been developed whereby alkyl glycidyl ethers can be produced in high yield from alcohols R'OH without necessity of isolating halohydrins (e.g. Japanese Laid-open Patent Applications Nos. 76508/79, 141708/79, 141709/79 and 141710/79). In order to obtain a glyceryl ether by the hydrolysis of the glycidyl ether, it is most effective to react the glycidyl ether with water with use of an acid catalyst. According to the results obtained from the studies by the present inventors, however, the reaction can hardly be conducted uniformly as the reaction system is a non-uniform system comprising water and oil, as shown in the comparative examples given hereinafter. Accordingly, in addition to the intended glyceryl ether, a great amount of polymers is produced as by-products as a result of the addition polymerization of the glycidyl ethers themselves. Thus, the yield of the glyceryl ether is lowered and the quality of the product is degraded. In order to obtain the glyceryl ether of high purity, a purification operation such as molecular distillation is required, and this makes it difficult to carry out the operation on an industrial scale.

SUMMARY OF THE INVENTION

Under these circumstances, the present inventors have made an extensive research to find out a method whereby α-monoalkyl glyceryl ethers are produced in good yield, in high purity and in a simple manner. In consideration of the facts that the glycidyl ether can easily be produced from an alcohol and that the production of the α-monoalkyl glyceryl ether by the hydrolysis of a 4-alkoxymethyl-1,3-dioxolan can easily be done, an idea has been conceived to combine the two processes for the production of the final α-monoalkyl glyceryl ether continuously from the starting alcohol.

It has been found unexpectedly that the idea can be reduced to practice by reacting an alkylglycidyl ether with a carbonyl compound in the presence of an acid catalyst, thereby to obtain a 4-alkoxymethyl-1,3-dioxolan in good yield. On the basis of this discovery, the present invention has been accomplished.

The process of the present invention is represented by the following reaction formulae:

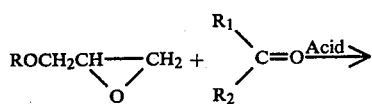

(I)

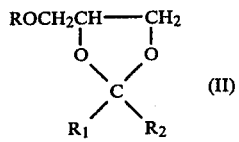

(II)

(where R is a saturated or unsaturated, straight chain or branched chain aliphatic hydrocarbyl group having from 8 to 24 carbon atoms, R₁ is a hydrogen atom or a hydrocarbyl group and R₂ is a hydrocarbyl group.)

The obtained 4-alkoxymethyl-1,3-dioxolan (II) is useful as an intermediate for the production of an α-monoalkyl glyceryl ether (III). The reaction for this production is represented by the following formula

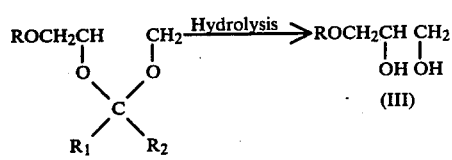

(III)

(where R, R₁ and R₂ are as defined above.)

DETAILED DESCRIPTION OF PREFERRED EMBODIMENTS OF THE INVENTION

The alkyl glycidyl ethers to be used in the present invention, have a straight chain or branched chain, saturated or unsaturated, primary, secondary or tertiary alkyl group having from 8 to 24 carbon atoms. Specific examples are straight chain primary alkyl glycidyl ethers such as n-octyl glycidyl ether, n-decyl glycidyl ether, n-dodecyl glycidyl ether, n-tetradecyl glycidyl ether, n-hexadecyl glycidyl ether, n-octadecyl glycidyl ether, n-octadecenyl glycidyl ether (oleyl glycidyl ether), and docosyl glycidyl ether; branched chain alkyl primary alkyl glycidyl ethers such as 2-ethylhexyl glycidyl ether, 2-hexyldecyl glycidyl ether, 2-octyldodecyl glycidyl ether, 2-heptylundecyl glycidyl ether, 2-(1,3,3-trimethylbutyl) octyl glycidyl ether, 2-decyltetradecyl glycidyl ether, 2-dodecylhexadecyl glycidyl ether, 2-tetradecyloctadecyl glycidyl ether, 5,7,7-trimethyl-2-(1,3,3-trimethylbutyl) octyl glycidyl ether and methyl branched isostearyl glycidyl ethers represented by the following formula:

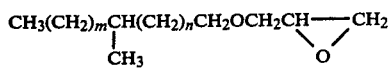

(where m+n=14, provided the distribution has its peak at m=n=7); secondary alkyl glycidyl ethers such as sec-decylglycidyl ether, sec-octyl glycidyl ether, and sec-dodecyl glycidyl ether; and tertiary alkyl glycidyl ethers such as t-octyl glycidyl ether, and t-dodecyl glycidyl ether.

If the final α-monoalkyl glyceryl ethers are to be used as emulsifiers, R in the starting glycidyl ether should preferably be a saturated or unsaturated, straight chain or branched chain primary alkyl group having from 12 to 20 carbon atoms, particularly 18 carbon atoms.

The carbonyl compounds to be used in the present invention, include ketones and aldehydes in general. As the ketones, there may be mentioned aliphatic ketones (such as acetone, methyl ethyl ketone, diethyl ketone, methyl propyl ketone, dipropyl ketone, ethyl propyl ketone, and methyl hexyl ketone), alicyclic ketones (such as cyclobutanone, cyclopentanone, cyclohexanone, and cyclooctanone) and aromatic ketones (such as acetophenone and benzophenone). As the aldehydes, there may be mentioned aliphatic aldehydes (such as formaldehyde, acetaldehyde, propionaldehyde, and octylaldehyde), alicyclic aldehydes (such as cyclopentylaldehyde, and cyclohexylaldehyde), and aromatic aldehydes (such as benzaldehyde and naphthylaldehyde). From the standpoint of easiness of the after treatments, lower carbonyl compound having a small number of carbon atoms are preferred, particularly those having at most 6 carbon atoms.

As the acid catalysts to be used for the production of the 4-alkoxymethyl-1,3-dioxolans (II), proton acids and Lewis acids may be used. As the proton acids, there may be mentioned sulfuric acid, hydrochloric acid, nitric acid and phosphoric acid. As the Lewis acids, there may be mentioned boron trifluoride etherate, boron trifluoride acetate complex, boron trifluoride phenol complex, aluminum chloride, aluminum bromide, zinc chloride, tin tetrachloride, antimony chloride, titanium tetrachloride, silicon tetrachloride, ferric chloride, ferric bromide, cobalt (II) chloride, cobalt (II) bromide, zirconium chloride, boron oxide and acid activated alumina.

It has been found that in order to produce the 4-alkoxymethyl-1,3-dioxolan from the alkyl glycidyl ether, generally the glycidyl ether may be reacted with from 1 to 30 moles of a carbonyl compound per mole of the glycidyl ether in the presence of from 0.001 to 0.2 mole of an acid catalyst at a temperature of from 0° to 70° C. The amount of the carbonyl compound to be used may theoretically be equivalent in the molar ratio to the glycidyl ether. In practice, however, the yield is better and the reaction proceeds more smoothly when an excess amount of the carbonyl compound is used, and accordingly, from 2 to 15 moles, more preferably about 7 moles, of the carbonyl compound per mole of the glycidyl ether, is used. The acid is used in a catalytic amount, i.e. from 0.001 to 0.3 mole, preferably from 0.01 to 0.1 mole, per mole of the glycidyl ether. This reaction is exothermic, and accordingly it is preferred to gradually add the carbonyl compound to the glycidyl ether together with the acid catalyst while adjusting the temperature not to exceed 60° C., and preferably to be within the range of from 20° to 40° C. by application of a proper cooling operation. If the reaction temperature is too high, it is possible that side reactions by the acid catalyst, such as cleavage of the epoxy bond or the ether bond of the glycidyl ether, or, in the case of a glycidyl ether containing an unsaturated bond, the isomerization of the unsaturated bond due to the acid catalyst or a Wagner-Meerwein type rearrangement reaction, occurs. Therefore, it is important to control the reaction temperature strictly. The reaction proceeds even in the absence of a reaction solvent, and accordingly, it is convenient to use an excess amount of the carbonyl compound as the solvent. However, it is possible to use a proper solvent for the purposes of suppressing the above mentioned side reactions, or controlling the reaction temperature. The reaction solvent may be any solvent which does not adversely affect the main reaction. Hydrocarbon solvents are preferred. As the hydrocarbon solvents, there may be mentioned an aliphatic hydrocarbon such as pentane, hexane, heptane, or octane, an aromatic hydrocarbon such as benzene, toluene or xylene, an alicyclic hydrocarbon such as cyclopentane or cyclohexane, or a mixture thereof.

If the reaction is carried out under the above mentioned conditions, the 4-alkoxymethyl-1,3-dioxolans are obtained usually in a yield of at least about 90%. If necessary, purification may be conducted e.g. by distillation. However, in most cases, they are obtained as a colourless, odourless, transparent liquid and accordingly they can be subjected to the next hydrolysis reaction as they are, without necessity of being subjected to isolation or purification.

The hydrolysis reaction of the 4-alkoxymethyl-1,3-dioxolans can be done by any known method. However, it is preferred to use a proton acid catalyst such as sulfuric acid, hydrochloric acid, nitric acid, phosphoric acid, perchloric acid, benzenesulfonic acid or acetic acid and to heat the reactant in water. There is no particular limitation with respect to the amount of the acid catalyst to be used. However, from 0.01 to 2N is usually sufficient, and particularly from 0.05 to 0.5N is suitable. It is preferred to add to the water, a water soluble organic solvent such as a lower alcohol e.g. methanol, ethanol, or isopropanol, THF or dioxane, and to carry out the reaction at a temperature of from 50° to 100° C. If the hydrolysis of the 4-alkoxymethl-1,3-dioxolan is carried out under these conditions, the final intended product of α-monoalkyl glyceryl ether can be obtained almost quantitatively. The formed α-monoalkyl glyceryl ether is usually separated from the water phase by leaving the reaction mixture to stand still. The separated one is collected, and the one dissolved in water can be recovered e.g. by extraction with use of a water isoluble organic solvent.

According to the present invention it is possible to obtain the 4-alkoxymethyl-1,3-dioxolans in good yield under a mild conditions from the alkyl glycidyl ethers which are more readily available than alcohols. Besides, it is possible to convert the 4-alkoxymethyl-1,3-dioxolans to α-monoalkyl glyceryl ethers almost quantitatively. Thus, it is possible to produce readily and in good yield the final intended products of α-monoalkyl glyceryl ethers from the starting alcohols.

The invention will be described in more detail with reference to the examples. It should be understood, however, that the present invention is not limited by these examples.

Example 1

(i) Into a round bottom flask having a capacity of 500 ml and equipped with a reflux condenser, a thermometer, a dropping funnel, a nitrogen gas supply tube, and a stirring means, 81.2 g (1.4 moles) of acetone, and 2.0 g (0.014 mole) of boron trifluoride etharate were charged and stirred while supplying a nitrogen gas. Then, 64.9 g (0.2 mole) of oleyl glycidyl ether was gradually added dropwise while supplying a nitrogen gas. The reaction mixture generates heat as the glycidyl ether is added. Therefore, the reaction mixture was cooled to maintain a temperature of from 20° to 30° C., and it took about one hour for the addition of the glycidyl ether. The stirring was continued for further one hour. After confirming by the gas chromatograph of the reaction mixture that the glycidyl ether completely disappeared, the reaction mixture was poured into a dilute aqueous solution of sodium bicarbonate whereby the acid was neutralized. Ether was added thereto and the mixture was stirred, and thereafter the ether layer was collected by separation. Anhydrous sodium sulfate was added for dehydration, and the solvent was removed by distillation under a reduced pressure thereby to obtain 68.8 g (yield: 90%) of colourless, transparent 2,2-dimethyl-4-oleyloxymethyl-1,3-dioxolan.

Boiling point: from 170° to 176° C. (0.07 mmHg)
IR (liquid film, cm$^{-1}$): 1380, 1370, 1260, 1215, 1120, 1080, 1060, 850, 721
NMR (CCl$_4$ solvent, δ):

5.3 (triplet, J = 5.0 Hz —CH=CH—)

3.3 to 4.4 (multiplet, RCH$_2$OCH$_2$CH     CH$_2$)

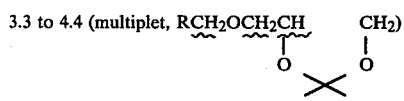

(ii) Into a reactor having a capacity of 1 liter and equipped with a stirring means, a thermometer, and a reflux condenser, 68.8 g (0.18 mole) of 2,2-dimethyl-4-oleyloxy-1,3-dioxolan obtained by (i) was charged, and 200 ml of ethanol and 200 ml of 0.1N sulfuric acid were added. While stirring, the mixture was heated and refluxed at a temperature of from 80° to 85° C. and after about 10 hours, it was confirmed by gas chromatograph that the hydrolysis of the 1,3-dioxolan compound was completely done. After being cooled, it was held to stand still, whereupon the water layer and oil layer were separated. The water layer was extracted with ether and the extract was combined with the previous oil layer. An aqueous sodium bicarbonate solution was added to neutralize the remaining acid. The organic layer was separated, and the solvent was removed under a reduced pressure. The heating and drying were continued for further 3 hours at 100° C./0.1 mmHg, whereupon 60.3 g (yield: 98%) of a colourless transparent liquid of α-monooleyl glyceryl ether was obtained.

IR (neat, cm$^{-1}$): 3400, 1050 to 1140
  It was found that this spectrum is identical with one described in Biochemistry Vol. 5, pages 618 to 625 (1966).
NMR (CCl$_4$ solvent, δ):

3.2 to 3.8 (multiplet, —CH$_2$OCH$_2$CH CH$_2$)
OH OH

Acid value: 0.07 (Theoretical: 0)
Saponification value: 0.09 (Theoretical: 0)
Hydroxyl value: 318 (Theoretical: 328)
Iodine value: 70 (Theoretical: 74)

Comparative Example 1

(i) Into a reactor having a capacity of 2 liters and equipped with a thermometer, a stirring means, a dropping funnel and Dean Stark trap, 317 g (2.4 moles) of 4-hydroxymethyl-2,2-dimethyl-1,3-dioxolan, 600 ml of xylene, 120 g (2.8 moles as NaOH) of 93% sodium hydroxide and 150 g of water, were charged, and heated and refluxed at a temperature of from 130° to 140° C. while stirring. From the distilled water/xylene mixture, water was separated in the Deans Stark trap and discharged out of the reaction system and the xylene was returned to the reaction system. After the heating and refluxing for about 6 hours, and when no more distillation of water was observed, 57.2 g (0.2 mole) of oleyl chloride was added dropwise from the dropping funnel for about 10 minutes. The reaction mixture was further heated and refluxed for 6 hours at 130° to 140° C. to complete the reaction. After cooling, sodium chloride precipitated in the reactor was removed by filtration whereby a blackish red oily substance was obtained. The solvent was removed under a reduced pressure and a distillation under a reduced pressure was carried out. Firstly, 2.5 g of a distillate having a boiling point of from 150° to 160° C. (from 2 to 3 mmHg) was obtained. This was identified to be an α-olefin as it showed an IR (neat) absorption at 3070, 3000, 1630, 990 and 905 cm$^{-1}$, which is derived from a terminal olefin. This showed that 5% as the α-olefin was formed. Then, 62.7 g (yield: 82%) of a distillate having a boiling point of from 160° to 174° C. (0.07 mmHg) was obtained. This was found to have the same IR, NMR spectrum of the 2,2-dimethyl-4-oleyloxy-1,3-dioxolan as obtained in Example 1.

(ii) Then, hydrolysis was carried out in the same manner as in (ii) of Example 1, whereupon 55 g (yield: 98%) of α-monooleyl glyceryl ether was obtained. This was found to have the same IR, NMR spectrum as obtained by Example 1 and its acid value, saponification value, hydroxyl value and iodine value were also the same.

Example 2

(i) The same reaction as in Example 1, was carried out, except that the oleyl grycidyl ether of Example 1 was replaced by stearyl glycidyl ether, whereupon 69.2 g (yield: 90%) of 2,2-dimethyl-4-stearoxy-1,3-dioxolan was obtained.

Boiling point: 178° to 182° C. (0.07 mmHg)
IR (neat, cm$^{-1}$): 1380, 1370, 1255, 1215, 1110, 1050, 850
NMR (CCl$_4$ solvent, δ):

3.3 to 4.4 (multiplet, 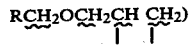)

1.34 (singlet)
1.40 (singlet)
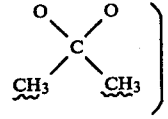

(ii) Then, hydrolysis was carried out in the same manner as in (ii) of the Example 1, whereupon 60.7 g (yield: 98%) of α-monostearyl glyceryl ether was obtained.
melting point: 70° to 71° C. (The value as described in Journal of Organic Chemistry, Vol. 29, pages 3055 to 3057, 1964: 71° to 71.5° C.)

Example 3

(i) The same reaction as in Example 1 was carried out except that the oleyl glycidyl ether of the Example 1 was replaced by isostearyl glycidyl ether [5,7,7-trimethyl-2-(1,3,3-trimethylbutyl) octyl glycidyl ether] (see Reference Example 1), whereupon 69.2 g (yield: 90%) of 4-(5,7,7-trimethyl-2-(1,3,3-trimethylbutyl) octyloxy)-2,2-dimethyl-1,3-dioxolan was obtained.

Boiling point: 128° to 135° C. (0.09 mmHg)
IR (neat, cm$^{-1}$): 1370, 1360, 1240, 1200, 1140, 1100, 1045, 840
NMR (CCl$_4$, δ):

3.2 to 4.3 (multiplet, 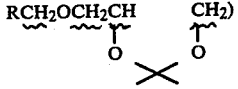)

1.28 (singlet)
1.33 (singlet)
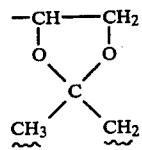

(ii) The obtained 1,3-dioxolan compound was subjected to hydrolysis in the same manner as in (ii) of Example 1, whereupon 61 g (yield: 98%) of colourless, transparent α-mono-(5,7,7-trimethyl-2-(1,3,3-trimethylbutyl) octyl) glyceryl ether was obtained.
IR (neat, cm$^{-1}$): 3400, 1105, 1040
NMR (CCl$_4$, δ):

3.2 to 3.8 (multiplet, RCH$_2$OCH$_2$CH CH$_2$)
                                    |    |
                                   OH  OH Acid value: 0.05 (Theoretical value: 0)
Saponification value: 0.20 (Theoretical value: 0)
Hydroxyl value: 320 (Theoretical value 326)
Iodine value: 0.03 (Theoretical value: 0)

Reference Example 1

Into a round bottom flask having a capacity of 1 liter and equipped with a reflux condenser, a thermometer, a dropping funnel, and a stirring means, 120 g of a 50% sodium hydroxide solution (60 g (1.5 mole) as pure sodium hydroxide), 68 g (0.25 mole) of isostearyl alcohol [5,7,7-trimethyl-2-(1,3,3-trimethylbutyl) octanol], 200 ml of n-hexane, and 2.51 g (0.0075 mole) of stearyl trimethyl ammonium chloride, were introduced in this order. The reaction mixture was kept at a reaction temperature of 25° C. in a water bath, and while vigorously stirring the mixture at a stirring speed of 400 r.p.m., 93 g (1 mole) of epichlorohydrin was added dropwise from the dropping funnel. It took about 1.5 hours for the addition of the epichlorohydrin, and the reaction mixture was heated to 50° C. and stirred for about 8 hours at this temperature. After the completion of the reaction, the mixture was treated in a usual manner, whereupon 67.9 g (yield: 83%) of isostearyl glycidyl ether (5,7,7-trimethyl-2-(1,3,3-trimethylbutyl)-octyl glycidyl ether) was obtained.
Boiling point: 117° to 121° C. (0.12 mmHg)
IR (neat, cm$^{-1}$): 3050, 3000, 1250, 1100, 910, 840
NMR (CCl$_4$, δ):

2.3 to 3.8 (multiplet, 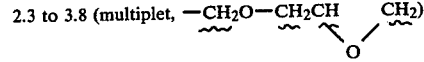)

Example 4

The same reaction as in Example 1 was carried out except that the oleyl glycidyl ether of Example 1 was replaced by isostearyl glycidyl ether (2-heptylundecyl glycidyl ether, see Reference Example 2), whereupon 68.2 g (yield: 90%) of 4-(2-heptylundecyloxy)-2,2-dimethyl-1,3-dioxolan was obtained.

Boiling point: 145° to 148° C. (0.03 mmHg)
IR (neat, cm$^{-1}$): 1375, 1365, 1250, 1210, 1140, 1105, 1050, 840
NMR (CCl$_4$, δ):

3.2 to 4.3 (multiplet, —CH$_2$OCH$_2$CHCH$_2$)

1.30 (singlet)

1.35 (singlet) (dioxolane ring with CH$_3$, CH$_3$)

(ii) The obtained 1,3-dioxolan compound was subjected to hydrolysis in the same manner as in Example 1, whereupon 60 g (yield: about 97%) of colourless, transparent α-mono (2-heptylundecyl)glyceryl ether was obtained.

IR (neat, cm$^{-1}$): 3400, 1110, 1040
NMR (CCl$_4$, δ):

3.2 to 4.0 (multiplet, —CH$_2$OCH$_2$CHCH$_2$)

Acid value: 0.03 (Theoretical: 0)
Saponification value: 0.15 (Theoretical: 0)
Hydroxyl value: 330 (Theoretical: 326)
Iodine value: 0.01 (Theoretical: 0)

Reference Example 2

The same reaction as in Reference Example 1 was carried out under the same conditions except that the 5,7,7-trimethyl-2-(1,3,3-trimethylbutyl) octanol in Reference Example 1 was replaced by 2-heptylundecanol, whereupon 65 g (yield: 80%) of 2-heptylundecyl glycidyl ether was obtained.

IR (neat, cm$^{-1}$): 3050, 3000, 1250, 1105, 910, 850
NMR (CCl$_4$, δ):

2.3 to 3.7 (multiplet, —CH$_2$OCH$_2$CH—CH$_2$ (epoxide))

Example 5

(i) The same reaction as in Example 1 was carried out under the same conditions except that the oleyl glycidyl ether of Example 1 was replaced by a monomethyl branched isostearyl glycidyl ether of the following formula, CH$_3$(CH$_2$)$_m$CH(CH$_2$)$_n$CH$_2$OCH$_2$CH—CH$_2$ (epoxide)
|
CH$_3$ (where m+n=14, provided the distribution has its peak at m=n=7; see Reference Example 3 for the production), whereupon 68 g (yield: 88%) of 4-monomethyl branched isostearoxymethyl-2,2-dimethyl-1,3-dioxolan was obtained.

Boiling point: 173° to 195° C. (0.40 mmHg)
IR (neat, cm$^{-1}$): 1200 to 1260, 1050 to 1120
NMR (CCl$_4$, δ):

3.1 to 4.2 (multiplet, —CH$_2$OCH$_2$CHCH$_2$)

(ii) The obtained 1,3-dioxolan compound was subjected to hydrolysis in the same manner as in (ii) of Example 1, whereupon 60 g (yield: 97%) of a colourless, transparent liquid of α-mono (monomethyl branched isostearyl) glyceryl ether was obtained.

IR (neat, cm$^{-1}$): 3400, 1100, 1040
NMR (CCl$_4$, δ):

3.2 to 3.8 (multiplet, RCH$_2$OCH$_2$CH CH$_2$)
                                        |   |
                                       OH OH Acid value: 0.08 (Theoretical: 0)
Saponification value: 0.36 (Theoretical: 0)
Hydroxyl value: 314 (Theoretical: 326)
Iodine value: 0.32 (Theoretical: 0)

Comparative Example 3

In a reactor having a capacity of 3 liters and equipped with a stirring means, a thermometer, a reflux condenser and a dropping funnel, 140 g of monomethyl branched isostearyl glycidyl ether (the same as the one used in Example 5) and 400 ml of diethylene glycol dimethyl ether were charged. While stirring the mixture, 800 ml of 0.5N sulfuric acid was added dropwise from the dropping funnel. After the addition, the mixture was heated at a temperature of from 100° to 110° C. and the heating and stirring were continued for about 8 hours at this temperature. It was found by gas chromatography that the glycidyl ether completely disappeared. The reaction product was cooled, and left to stand still, whereby the oil layer and the water layer were separated. The water layer was extracted with ether and the extract was added to the previously obtained oil layer. The remaining acid was neutralized with an addition of sodium bicarbonate. The oil layer was separated, and the solvent was removed under a reduced pressure. The heating and drying were further carried out for 3 hours at 100° C./0.1 mmHg, whereupon 120 g of a colourless, transparent liquid was obtained. The IR and NMR of this liquid were similar to those of α-mono (monomethyl branched isostearyl) glyceryl ether obtained in Example 5. However, the hydroxyl value thereof was 200 (theoretical value being 326). This shows that a greater amount of an addition polymerization product of the glycidyl ether itself was formed by a side reaction.

Reference Example 3

The same reaction as in Reference Example 1 was carried out under the same conditions except that the 5,7,7-trimethyl-2-(1,3,3-trimethylbutyl) octanol was replaced by a monomethyl branched isostearyl alcohol (CH$_3$(CH$_2$)$_m$CH(CH$_2$)$_n$—CH$_2$OH,
|
CH$_3$ where m+n=14, the distribution having its peak at m=n=7, see Reference Example 4 for the production), whereupon 68 g (yield: 83%) of a monomethyl branched isostearyl glycidyl ether was obtained.

Boiling point: 142° to 175° C. (0.08 mmHg)
IR (neat, cm$^{-1}$): 3050, 3000, 1250, 1100, 920, 845

Reference Example 4

Into a 20 liter autoclave, 4770 g of isopropyl isostearate ester [Emery 2310 isopropyl isostearate ester, sold by Emery Industries, USA] and 230 g of a copper-chromium catalyst (made by Nikki) were charged. Then, the inside was filled with hydrogen gas under a pressure of 150 kg/cm², and the reaction mixture was heated to 275° C. Hydrogenation was carried out for about 7 hours at 150 kg/cm²/275° C. Then, the reaction product was cooled, and the catalyst residue was removed by filtration, whereupon 3500 g of a crude product was obtained. The crude product was distilled under a reduced pressure, whereupon 3300 g of colourless, transparent isostearyl alcohol was obtaiend as a distilate at 80° to 167° C./0.6 mmHg. The obtained isostearyl alcohol (monomethyl branched isostearyl alcohol) had an acid value of 0.05, a saponification value of 5.5, a hydroxyl value of 181.4. An absorption was shown at 3340 and 1055 cm$^{-1}$ in IR (neat) and at $\delta$ 3.50 (broad triplet, 13 CH$_2$—OH) in NMR (CCl$_4$ solvent). This alcohol was found by gas chromatography to comprise about 75% of the principal component containing alkyl groups having a total carbon number of 18 (the total of m plus n in the formula being 15), and the rest of the components having a total carbon number of 14 or 16. It was found that it was a mixture of those in which the branched methyl group was always located in the vicinity of the central portion of the main alkyl chain.

Example 6

(i) The same reaction as in Example 1 was carried out under the same conditions except that in place of the boron trifluoride etherate, 1.0 g (about 0.01 mole) of concentrated sulfuric acid was used, whereupon 69.3 g (91%) of 2,2-dimethyl-4-oleyloxy 1,3-dioxolan was obtained.

(ii) Then, the dioxolan compound was subjected to hydrolysis in the same manner as in (ii) of Example 1, whereupon 60 g (yield: 98%) of oleyl glyceryl ether was obtained. This showed the same physical properties as those of the glyceryl ether obtained in Example 1.

What is claimed is:

1. A process for the production of an α-monoalkyl-glyceryl ether represented by the formula (III):

where R is a saturated or unsaturated, straight chain or branched chain aliphatic hydrocarbyl group having from 8 to 24 carbon atoms, which process is characterized in that an alkyl glycidyl ether represented by the formula (I):

where R is as defined above and a carbonyl compound of formula R$_1$COR$_2$ wherein R$_1$ is a hydrogen atom or hydrocarbyl group and R$_2$ is a hydrocarbyl group respectively are reacted in the presence of a Lewis acid catalyst, to obtain a 4-alkoxymethyl-1,3-dioxolan represented by the formula (II):

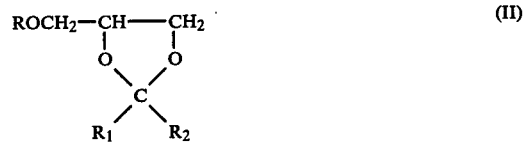

where R is as defined above, R$_1$ and R$_2$ are as defined above, and said alkoxymethyl-1,3-dioxolan is then hydrolyzed to said α-monoalkyl-glyceryl ether, said alkyl glycidyl ether and the carbonyl compound being reacted in a molar ratio of 1:1–30, the Lewis acid catalyst being employed in an amount of 0.001–0.2 mole per mole of alkyl glycidyl ether, and the reaction temperature being 0°–70° C.

* * * * *